United States Patent
Eriksson et al.

(10) Patent No.: US 8,525,535 B2
(45) Date of Patent: Sep. 3, 2013

(54) TEST BODY, TEST ARRANGEMENT, METHOD FOR MANUFACTURING OF A TEST BODY, AND METHOD FOR DETERMINING A MOISTURE CONTENT OF THE INSULATION OF A POWER TRANSFORMER DURING DRYING THEREOF

(75) Inventors: Thomas Eriksson, Balinge (SE); Uno Gafvert, Vasteras (SE)

(73) Assignee: ABB Technology Ltd. (CH)

( * ) Notice: Subject to any disclaimer, the term of this patent is extended or adjusted under 35 U.S.C. 154(b) by 0 days.

(21) Appl. No.: 12/958,034

(22) Filed: Dec. 1, 2010

(65) Prior Publication Data
US 2011/0115506 A1    May 19, 2011

Related U.S. Application Data

(63) Continuation of application No. PCT/EP2009/057407, filed on Jun. 16, 2009.

(30) Foreign Application Priority Data
Jun. 26, 2008 (EP) .................... 08159112

(51) Int. Cl.
*G01R 27/08* (2006.01)
(52) U.S. Cl.
USPC ........... 324/694; 200/86 R; 200/512; 73/73; 73/29.05; 210/23 R
(58) Field of Classification Search
USPC ............. 324/551–554, 664, 667, 688, 689, 324/694; 73/73, 74
See application file for complete search history.

(56) References Cited

U.S. PATENT DOCUMENTS

| | | | | |
|---|---|---|---|---|
| 3,243,540 | A * | 3/1966 | Miller | 200/86 R |
| 3,961,246 | A * | 6/1976 | Waterman et al. | 324/547 |
| 4,047,239 | A * | 9/1977 | Waterman et al. | 324/547 |
| 4,272,986 | A * | 6/1981 | Lowry et al. | 73/73 |
| 4,651,121 | A * | 3/1987 | Furubayashi et al. | 338/35 |
| 4,768,012 | A * | 8/1988 | Williams et al. | 338/34 |
| 5,546,974 | A * | 8/1996 | Bireley | 137/78.3 |
| 5,801,307 | A * | 9/1998 | Netzer | 73/170.17 |
| 6,222,376 | B1 * | 4/2001 | Tenney, III | 324/664 |
| 6,323,659 | B1 * | 11/2001 | Krahn | 324/664 |

(Continued)

FOREIGN PATENT DOCUMENTS
WO   2008026997 A1   3/2008

OTHER PUBLICATIONS

International Search Report and Written Opinion of the International Searching Authority; PCT/EP2009/057407; Sep. 7, 2009; 9 pages.

*Primary Examiner* — Melissa Koval
*Assistant Examiner* — Benjamin M Baldridge
(74) *Attorney, Agent, or Firm* — St. Onge Steward Johnston & Reens LLC

(57) ABSTRACT

A test body for use in determining moisture content in a laminated insulation of a power transformer by measuring a dielectric frequency response of the test body. The test body has a laminated structure of the same material as the laminated insulation, and has a shape and a size to obtain moisture content characteristics that resembles the moisture content characteristics of the laminated power transformer insulation. The test body further includes electrodes, which are embedded in the laminated structure.

16 Claims, 2 Drawing Sheets

(56) References Cited

U.S. PATENT DOCUMENTS

| | | | |
|---|---|---|---|
| 6,779,385 B2 * | 8/2004 | Belanger | 73/73 |
| 6,870,374 B2 * | 3/2005 | Perkins et al. | 324/551 |
| 6,883,371 B2 * | 4/2005 | Sugaya et al. | 73/335.05 |
| 7,210,333 B2 * | 5/2007 | Fujita et | 73/29.05 |
| 7,222,531 B2 * | 5/2007 | Isogai et al. | 73/335.04 |
| 7,340,952 B2 * | 3/2008 | Tanida | 73/335.02 |
| 7,554,051 B2 * | 6/2009 | Crispin | 200/512 |
| 7,688,215 B2 * | 3/2010 | Vokey et al. | 340/604 |
| 7,777,262 B2 * | 8/2010 | Izumi | 257/296 |
| 8,071,030 B2 * | 12/2011 | Bhullar et al. | 422/82.01 |
| 2003/0179805 A1 * | 9/2003 | Hamamoto et al. | 374/16 |
| 2004/0178069 A1 * | 9/2004 | Wang et al. | 204/408 |
| 2006/0055502 A1 * | 3/2006 | Usui | 338/34 |
| 2006/0144704 A1 * | 7/2006 | Ghesquiere et al. | 204/403.01 |
| 2006/0290360 A1 * | 12/2006 | Lee | 324/690 |
| 2007/0273394 A1 * | 11/2007 | Tanner et al. | 324/664 |
| 2008/0278336 A1 * | 11/2008 | Ortega et al. | 340/573.5 |
| 2011/0291674 A1 * | 12/2011 | Hosokawa | 324/658 |

* cited by examiner

TEST BODY, TEST ARRANGEMENT, METHOD FOR MANUFACTURING OF A TEST BODY, AND METHOD FOR DETERMINING A MOISTURE CONTENT OF THE INSULATION OF A POWER TRANSFORMER DURING DRYING THEREOF

CROSS-REFERENCE TO RELATED APPLICATIONS

The present application is a continuation of pending International patent application PCT/EP2009/057407 filed on Jun. 16, 2009 which designates the United States and claims priority from European patent application EP 08159112.5 filed on Jun. 26, 2008, the content of which is incorporated herein by reference.

FIELD OF THE INVENTION

The present invention relates to a test body for use in determining a moisture content in a laminated insulation of a power transformer. Further, the invention relates to a test arrangement including the above test body and to a method for manufacturing the test body.

Yet further, the invention relates to a method for determining a moisture content in a laminated insulation of a power transformer during or after drying thereof. Preferably, the determination of moisture content is based on a measurement of dielectric frequency response, that is, a measurement of frequency dependence of capacitance or permittivity and dielectric losses.

BACKGROUND OF THE INVENTION

During the manufacturing of power transformers the insulation, paper windings as well as insulation made of wood or cellulose, will adopt a certain level of humidity depending on the humidity of the surrounding atmosphere. Normally, the insulation material will adopt a humidity of approximately 5-8 percent when being exposed to free air during the production of the power transformer.
However, under operational conditions, the humidity of the insulation material should be as low as approximately 0.5 percent in order to guarantee the required insulation properties. Therefore, the manufacturing of power transformers includes a drying step, during which the transformer is subjected to vacuum and heat, and, depending on the specific technique being used, a vapor phase treatment or circulated hot air and vacuum, in order to lower the humidity of the electric insulation.

According to prior art, during the drying process of power transformers, the length of the process is defined by measuring the extraction of water during the vacuum treatment. The process is stopped when a predetermined water extraction value (for example expressed in ml water per ton insulation and hour) is reached. This method has the disadvantage of not being a measurement of the real humidity in the insulation, but a measurement of the removed amount of water only. Moreover, should there be a certain part of the insulation that dries more slowly than the major part of the insulation, prior art might not be enough precise and not able to determine the momentary humidity of such a part. Therefore, in order to guarantee that a required level of humidity is reached, an excessive length of vacuum treatment needs to be applied.

WO 2008/026997 discloses a method of determining the moisture content in a part of the insulation of a power transformer, which addresses the above problem. The method comprises the following steps: providing a test body, the moisture content characteristics of which corresponds to the moisture content characteristics of the part of the power transformer insulation, subjecting the test body to an atmosphere corresponding to the one that the part of the power transformer insulation is subjected to, determining the moisture content of the test body by means of measurement of dielectric frequency response thereof, and determining the moisture content of the part of the power transformer insulation upon basis of the determined moisture content of the test body. The measurement is performed by applying voltage plates on opposite sides of the test body and applying a voltage across the test body.

SUMMARY OF THE INVENTION

It has been noted that the above approach does not work properly. In particular, the measurement does not provide reliable results.

It is therefore an object of the invention to provide a test body, a test arrangement, and a method by means of which the need of drying the insulation of a power transformer during the drying process can be determined accurately and with precision.

Further, it is an object of the invention to provide a test body, a test arrangement, and a method, which allow for shortened drying times the insulation of a power transformer, which results in shortened production time of the power transformer.

Yet further, it is an object of the invention to provide a method for manufacturing a test body, which fulfills the above objects.

These objects, among others, are attained by test bodies, a test arrangement, test body manufacturing methods, and methods for determining moisture content as defined in the appended patent claims.

According to a first aspect of the invention there is provided a test body for use in determining a moisture content in a laminated insulation of a power transformer by means of measuring a dielectric frequency response of the test body. The test body has a laminated structure of the same material as said laminated insulation, has a shape and a size to obtain moisture content characteristics that resembles the moisture content characteristics of said laminated insulation, and comprises further electrodes, which are embedded in the laminated structure.

Preferably, the laminated structure comprises a plurality of plates such a cellulose pressboard sheets adhered to one another, wherein the electrodes are formed as thin layers on one or more of the cellulose pressboard sheets.

By means of the invention more accurate and precise measurements of the moisture content in the laminated insulation of a power transformer are achieved. Hereby the drying process can be optimized and the entire transformer production will be faster and cheaper.

According to a second aspect of the invention there is provided a test arrangement, which includes the test body of the first aspect of the invention.

According to a third aspect of the invention there is provided a method for manufacturing a test body for use in determining a moisture content in a laminated insulation of a power transformer by means of measuring a dielectric frequency response of the test body. According to the method electrodes are formed on one or more surfaces of one or more of a plurality of plates or sheets made of the same material as the laminated insulation. The plurality of plates is then laminated together, wherein the electrodes become embedded in the laminates structure. The shape and size of the laminated structure is selected to obtain moisture content characteristics of the laminated structure that resembles the moisture content characteristics of the laminated insulation of the power transformer.

Preferably, the electrodes are formed by means of printing or painting one or more conductive patterns on the one or more surfaces of the one or more plates.

According to a fourth aspect of the invention there is provided a method for determining a moisture content in a laminated insulation of a power transformer during or after drying thereof. According to the method a laminated test body with electrodes embedded therein is provided, wherein the moisture content characteristics of the test body corresponds to the moisture content characteristics of the laminated insulation of the power transformer. A device for measuring the dielectric frequency response is connected to the electrodes. The test body is subjected to an atmosphere corresponding to the atmosphere that the laminated power transformer insulation is subjected to. Next, the moisture content of the test body is determined by means of measuring the dielectric frequency response thereof, and finally, the moisture content of the laminated power transformer insulation is determined based on the determined moisture content of the test body.

Preferably, the measurement of the frequency dependence of capacitance or permittivity and dielectric losses in the test body is an online measurement, performed during the drying process.

Yet preferably, the test body is subjected to an atmosphere corresponding to the atmosphere that the laminated power transformer insulation is subjected to during the entire drying step and optionally during previous steps of mounting the laminated transformer insulation.

Further characteristics of the invention and advantages thereof, will be evident from the detailed description of preferred embodiments of the present invention given hereinafter and the accompanying FIGS. 1-7, which are given by way of illustration only and thus, are not limitative of the present invention.

DETAILED DESCRIPTION OF THE INVENTION

Figure 1:
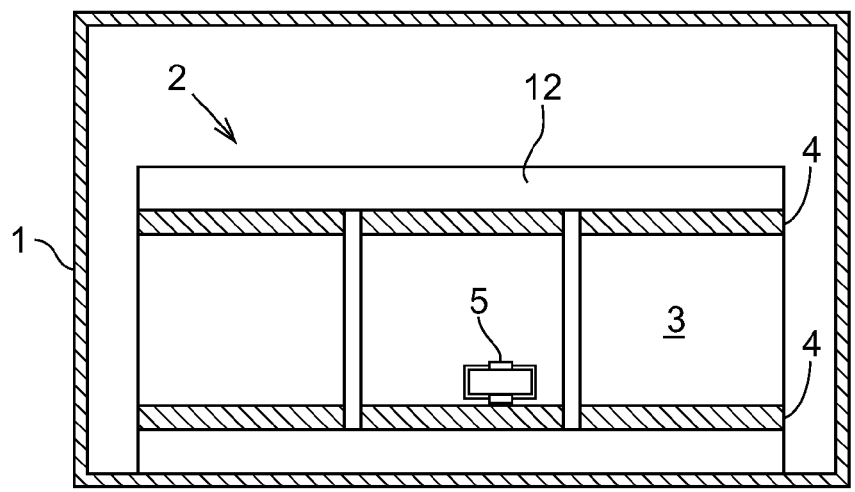
FIG. 1 is a schematic side view of a power transformer located in a vacuum tank during a drying step, and a test arrangement according to the invention.

FIG. 1 shows a tank 1 in which the active part 2 of a power transformer is located in a drying step during the production of a power transformer. The active part 2 of the power transformer comprises paper-insulated copper conductors, pressboard details, etc. schematically indicated by reference numeral 3, and bottom and top insulation parts 4, each being comprised of a laminate structure of compressed cellulose plates, so-called cellulose pressboard. Further, a transformer core or transformer core sheet 12 is also shown as part of the active part 2 of the transformer.

During the drying step, vacuum is generated in the tank or container 1, while, simultaneously, the power transformer is subjected to a vapor phase heating, in order to lower the humidity of the electric insulation. Normally, the insulation material will have adopted a humidity of approximately 5-8 percent upon previously being exposed to free air during the production of the power transformer.

The drying of the active part 2 of the transformer is due to the fact that, under operational conditions, the humidity of the insulation material should be as low as approximately 0.5 percent in order to guarantee the required insulation properties.

Figure 2:
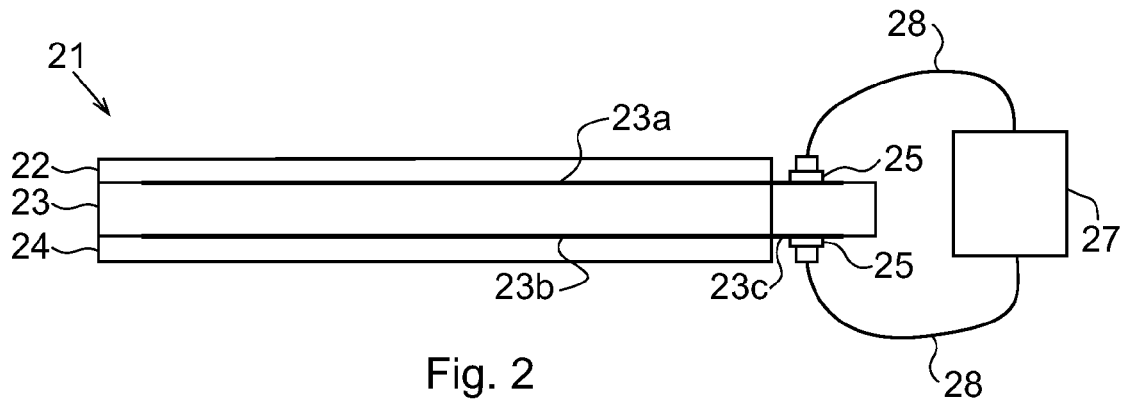
FIGS. 2-3 are more detailed schematic side and top views of the test arrangement of FIG. 1.
Figure 3:
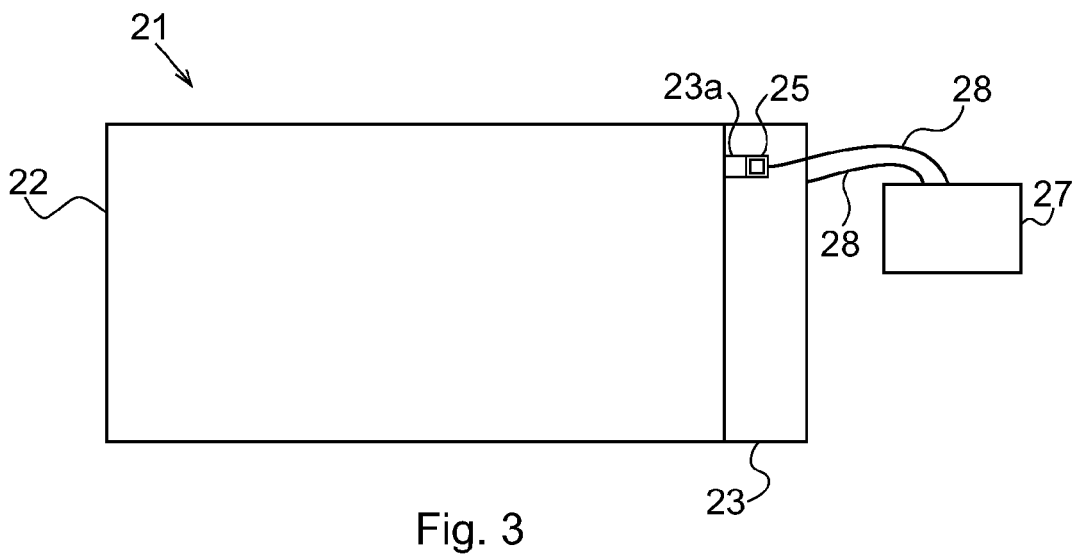
Figure 4:
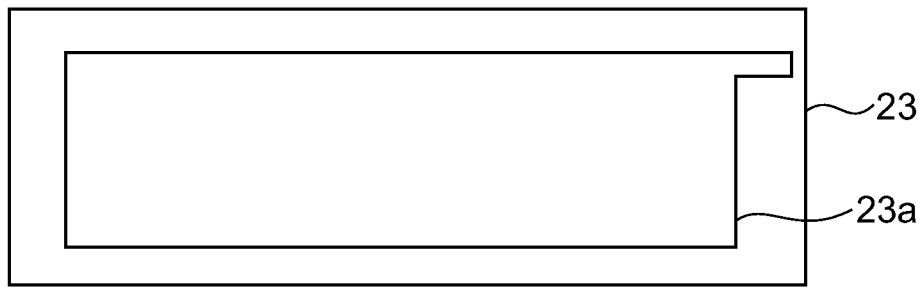
FIG. 4 is a schematic top view of an electrode formed on a plate of a test body as being comprised in the test arrangement of FIG. 2.

Together with the active part 2 in the tank 1 there is also provided a test arrangement, which is detailed in FIGS. 2-3. The test arrangement 5 includes a test body or sample 21 and a test device 27 provided with connectors 28 for determining a moisture content of the test body 29.

The test body 21 is made of a material corresponding to that of the electric insulation parts 4, namely a structure of at least three compressed cellulose plates 22, 23, 24, cellulose pressboard, adhered to each other, for example by means of a PE-glue. It has a geometry, for example thickness, corresponding to the one of that part of the electric insulation parts 4 that, upon experimental basis and experience, is known to have the highest moisture content and/or the slowest drying rate upon drying. Moreover, it has drying characteristics, especially a drying rate, that resembles or corresponds to the electric insulation parts 4.

The test body 21 comprises further electrodes 23a-b, which are embedded in the laminated structure of the test body 21. Preferably, the electrodes 23a-b are layers formed on one or more surfaces of the cellulose plates 22, 23, 24, for example, one electrode 23a may be formed on an upper side of one of the plates such as the electrode 23 located in the middle, whereas the other electrode 23b may be formed on the bottom side of that plate 23.

The plate 23, on whose surfaces the electrodes 23a-b are formed, is longer than the other ones of the plates 22, 24; and has an end portion 23c, which is protruding from the other ones of the plates 22, 24 and is provided with electrode connectors 25 for the electrodes 23a-b.

The test body 21 may be manufactured by forming the electrodes 23a-b on the surfaces of the plate 23 by means of e.g. printing or painting more conductive patterns thereon. Thereafter, the electrodes 23a-b are embedded in the test body 21 by means of laminating together the three plates 22-24 with the plate carrying the electrodes as the middle one.

Prior to the measurement of the moisture content the connectors 28 of the test device 27 are connected to the connectors 25 of the test body. The test device 27 is preferably a device for measuring the dielectric frequency response and may be known per se. The test device 27 is provided for applying a voltage across the electrodes 23a-b at a frequency in the range 1 mHz-10 kHz. During the measurement the test body 21 is subjected to same atmosphere as the electric insulation parts 4 is subjected to. Preferably, the test body 21 is subjected to the same atmosphere as the electric insulation parts 4 during the entire drying of the electric insulation parts 4 of the power transformer, and most preferably, the test body is subjected to the same atmosphere as the electric insulation parts 4 during the step of mounting the electric insulation parts 4 of the power transformer, which is made prior to the drying step. Hereby, it can be ensured that the test body 21 will have the same moisture content characteristics as the electric insulation parts 4.

The moisture content of the test body 21 is repeatedly or continuously determined by means of repeatedly or continuously measuring the dielectric frequency response thereof by the test device 27, and the moisture content of the electric insulation parts 4 is determined based on the determined moisture content of the test body 21.

A computer (not illustrated) may be integrated in or connected to the test device 27 and may be provided with software adapted for the execution of the dielectric frequency response and the presentation of the results thereof. Preferably, the measured dielectric response value is compared to referential dielectric response values for different moisture contents previously determined for the test body 21 or similar body. The measured signature may, alternatively, be compared to calculated theoretical dielectric frequency responses.

The comparing may include comparing the shape of one or more graphical representations of the dielectric frequency response with reference graphical representations.

It should be understood that the test device 27 may comprise all equipment necessary for performing the steps of a conventional dielectric frequency response measurement for the purpose of measuring the moisture content of the test body 21 and thus the moisture content of the electric insulation parts 4 of the power transformer.

It shall be appreciated that a control apparatus (not illustrated) may be connected to the test device 27 in order to be repeatedly supplied with moisture content figures and configured to dynamically control the drying of the electric insulation parts 4 of the power transformer in response thereto.

Figure 5:
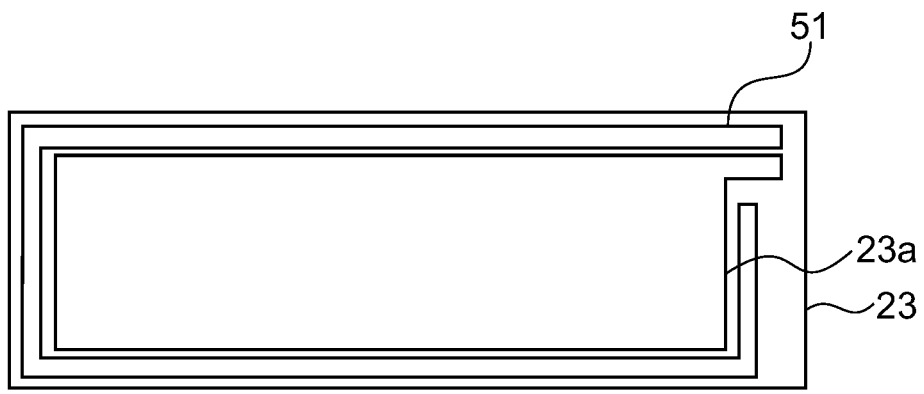
FIG. 5 is a schematic top view of an electrode arrangement formed on a plate of a test body according to an alternative embodiment of the invention.

FIG. 5 shows an electrode layer arrangement formed on a plate 23 of a test body according to an alternative embodiment of the invention. This electrode arrangement replaces one of the electrodes in the previous embodiment and includes one centrally located patch electrode layer 23 used for applying the above mentioned voltage and an outer strip electrode layer 51, which surrounds the patch electrode layer 23a, and operates as a guard electrode for control of the electric field obtained by the applied voltage. Hereby, the measurement can be made more reliable and/or the precision in the measurement can be improved.

Figure 6:
FIGS. 6-7 are each a schematic side view of a test body according to yet an alternative embodiment of the invention.
Figure 7:
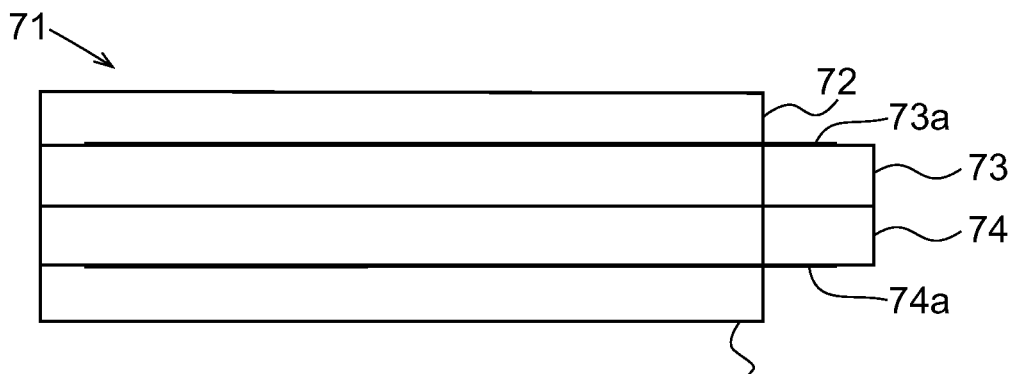

FIGS. 6 and 7 show each a test body according to yet an alternative embodiment of the invention. The test body 61 of FIG. 6 comprises a laminated structure of two cellulose plates 62, 63, wherein electrode layers 63a-63b are formed on the upper surface of the lower plate 63. The electrode layers are formed with appropriate patterns to obtain connections at an end portion of the lower plate 63. The test body 71 of FIG. 7 comprises a laminated structure of four cellulose plates 72, 73, 74, 75, wherein electrode layers 73a, 74a are formed on different surfaces of different ones 73, 74 of the plates. The electrode layers are formed with appropriate patterns to obtain connections at end portions of the plates 73, 74.

It shall be appreciated that while various embodiments of the test body have been described, the invention is not limited to such embodiments. In particular, the test body of the invention may comprise more laminated layers, have different geometry, and be of a different material. Similarly, the electrodes may have different patterns, be located differently, and be of different numbers.

What is claimed is:

1. A test body for use in determining a moisture content in a laminated insulation of a power transformer by means of measuring a dielectric frequency response of said test body, said test body comprising:
    a laminated structure of the same material as said laminated insulation of the power transformer, said laminated structure having a shape and a size to obtain moisture content characteristics that resembles the moisture content characteristics of said laminated insulation of the power transformer, wherein the laminated structure further comprises:
    a plurality of plates, made of the same material as said laminated insulation of the power transformer, adhered to one another, the plurality of plates having an at least one top plate, an at least one bottom plate and at least one middle plate, the at least one middle plate being longer than the at least one top plate and the at least one bottom plate, the at least one middle plate having an end portion protruding past the at least one top plate and the at least one bottom plate;
    at least one electrode embedded in said laminated structure, the at least one electrode forming at least one layer on one or more surfaces of at least one middle plate, the at least one middle plate supporting section of said at least one electrode; and
    electrode connectors directly connected to said at least one electrode arranged on the end portion of the at least one middle plate, the electrode connectors being directly connected to connectors of a test device.

2. The test body of claim 1, wherein said plates are cellulose pressboards.

3. The test body of claim 1, wherein said at least one electrode includes at least two electrodes formed on different surfaces of the at least one middle plates.

4. The test body of claim 1 wherein said at least one electrode includes at least two electrodes formed on a single surface of the at least one middle plate.

5. The test body of claim 1 wherein a guard electrode layer is formed on one or more surfaces of the at least one middle plate.

6. The test body of claim 5, wherein the guard electrode layer surrounds the electrodes embedded in said laminated structure and controls the electric field obtained by an applied voltage.

7. The test body of claim 5, wherein the guard electrode layer surrounds a centrally located patch electrode layer for control of the electric field obtained by the applied voltage.

8. The test body of claim 5, wherein the guard electrode layer is an outer trip electrode layer.

9. A test arrangement including the test body of claim 1 and further including means for measuring a dielectric frequency response of the test body.

10. The test body of claim 1, wherein the laminated structure and the test body are moisture sensitive.

11. A method for manufacturing a test body for use in determining a moisture content in a laminated insulation of a power transformer by means of measuring a dielectric frequency response of said test body, said method comprising the steps of:
    forming at least one electrode on one or more surfaces of an at least one middle plate of the same material as said laminated insulation of the power transformer prior to a step of lamination, the at least one middle plate supporting sections of said at least one electrode, and
    laminating together a plurality of plates of the same material as said laminated insulation of the power transformer and of a shape and a size to obtain moisture content characteristics of the plurality of plates laminated together that resembles the moisture content characteristics of said laminated insulation of the power transformer, the plurality of plates having a top plate, a bottom plate and the at least one middle plate, the at least one middle plate being longer that the top plate and the bottom plate, the at least one middle plate having an end portion protruding past the top plate and the bottom plate, wherein the step of laminating comprises the step of embedding said electrodes in said plurality of plates laminated together, and further comprises the step of embedding said electrodes in said plurality of plates laminated together, and providing electrode connectors for said at least one electrode arranged on the end portion of the at least one middle plate, the electrode connectors being connected to connectors of a test device.

12. The method of claim 11 wherein said at least one electrode is formed on said one or more surfaces of said one or more of the plates by means of printing or painting one or more conductive patterns thereon.

13. A method for determining a moisture content in a laminated insulation of a power transformer during or after drying thereof, comprising the steps of:

providing a laminated test body having a plurality of plates made of the same material as said laminated insulation of the power transformer adhered to one another, the plurality of plates having a top plate, a bottom plate and at least one middle plate, the middle plate being longer than the top plate and the bottom plate, the at least one middle plate having an end portion protruding past the top plate and the bottom plate, the plurality of plates having electrodes embedded therein, the electrodes being layers formed on one or more surfaces of the plates, the at least one middle plate supporting sections of the electrodes, wherein the moisture content characteristics of said test body corresponds to the moisture content characteristics of said laminated insulation;

connecting a test device for measuring the dielectric frequency response to said electrodes;

subjecting said test body to an atmosphere corresponding to an atmosphere that said laminated insulation of the power transformer is subjected to;

determining the moisture content of said test body by means of measuring the dielectric frequency response thereof, and determining the moisture content of said laminated insulation of the power transformer based on the determined moisture content of said test body, wherein said end portion of the at least one middle plate supports sections of said electrodes and is provided with electrode connectors directly coupled to said electrodes.

14. The method of claim 13 wherein said test body is subjected to the same atmosphere as said laminated insulation of the power transformer during the entire drying of the laminated insulation of the power transformer.

15. The method of claim 13 wherein said test body is subjected to the same atmosphere as said laminated insulation of the power transformer during the step of mounting the laminated insulation of the power transformer.

16. A test body for use in determining a moisture content in a laminated insulation of a power transformer by means of measuring a dielectric frequency response of said test body, said test body comprising:

a laminated structure made of the same material as said laminated insulation of the power transformer, said laminated structure having a shape and a size to obtain moisture content characteristics that resembles the moisture content characteristics of said laminated insulation;

two plates made of the same material as said laminated insulation of the power transformer adhered to one another as part of the laminated structure, the two plates including a lower plate and an upper plate;

electrodes embedded in said laminated structure, said electrodes being layers formed on an upper surface of the lower plate, wherein the lower plate, on whose surfaces said electrodes are formed, is longer than the upper plate, the lower plate having an end portion protruding past the top plate and having electrode connectors for said electrodes on the end portion.

* * * * *